United States Patent
Holoshitz et al.

(10) Patent No.: US 6,518,259 B1
(45) Date of Patent: Feb. 11, 2003

(54) COMPOSITIONS FOR TREATING AUTOIMMUNE DISEASE

(75) Inventors: Joseph Holoshitz; James A. Shayman; Shi-Yu Tan, all of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/575,612

(22) Filed: May 22, 2000

Related U.S. Application Data

(62) Division of application No. 09/009,906, filed on Jan. 21, 1998, now Pat. No. 6,098,631.

(51) Int. Cl.$^7$ .................. A61K 31/66; A61K 31/70; A61K 31/14

(52) U.S. Cl. ............... 514/114; 514/24; 514/44; 514/642

(58) Field of Search ............... 514/114, 24, 44, 514/642; 435/6, 15

(56) References Cited

U.S. PATENT DOCUMENTS

| | | | |
|---|---|---|---|
| 5,137,919 A | 8/1992 | Igarashi et al. | 514/642 |
| 5,151,360 A | 9/1992 | Handa et al. | 435/240.2 |
| 5,248,828 A | 9/1993 | Saito et al. | 568/33 |
| 5,260,288 A | 11/1993 | Igarashi et al. | 514/114 |
| 5,331,014 A | 7/1994 | Kimura et al. | 514/642 |
| 5,391,800 A | 2/1995 | Igarashi et al. | 558/145 |
| 5,466,716 A | 11/1995 | Igarashi et al. | 514/642 |
| 5,583,160 A | 12/1996 | Igarashi et al. | 514/669 |
| 5,627,171 A | 5/1997 | Park et al. | 514/114 |
| 5,663,313 A | 9/1997 | Hawkins et al. | 536/23.1 |
| 5,663,314 A | 9/1997 | Segar et al. | 566/23.2 |
| 5,677,189 A | 10/1997 | Igarashi et al. | 436/57 |
| 5,712,262 A | 1/1998 | Spiegel | 514/114 |
| 5,834,479 A * | 11/1998 | Mayer et al. | 514/289 |
| 5,871,930 A | 2/1999 | Bandman et al. | 435/6 |
| 6,190,894 B1 * | 2/2001 | Thornfeldt et al. | 435/183 |

OTHER PUBLICATIONS

R. Million et al., "Long–Term Study of Management of Rheumatoid Arthritis," *Lancet* 1:812–816 (1984).

J. A. Engelbrecht et al., "Methotrexate Pneumonitis After Low–Dose Therapy for Rheumatoid Arthritis," *Arthritis and Rheumatism* 26(10):1275–1278 (1983).

G. W. Cannon et al., "Acute Lung Disease Associated WIth Low–Dose Pulse Methotrexate Therapy In Patients With Rheumatoid Arthritis," *Arthritis and Rheumatism* 26(10):1269–1274 (1983).

Simon and Mills, "Nonsteroidal Antiinflammatory Drugs," *N. Eng. J. Med.* 302(21):1179–1243 (1980).

W. Katz et al., "Proteinuria in Gold–Treated Rheumatoid Arthritis," *Ann. Int. Med.* 101:176–179 (1984).

W. F. Kean et al., "The Toxicity Pattern Of D–Penicillamine Therapy," *Arthritis and Rheumatism* 23(2):158–164 (1980).

S. Nagata, "Fas and Fas Ligand: A Death Factor and Its Receptor," *Advances in Immunology* 57:129–144 (1994).

R. N. Kolesnick et al., "The Sphingomyelin Signal Transduction Pathway Mediates Apoptosis For Tumor Necrosis Factor, Fas, and Ionizing Radiation," *Biochem. Cell Biol.* 72:471–474 (1994).

M. Verheij et al., "Requirement for ceramide–initiated SAPK/JNK signaling in stress–induced apoptosis," *Nature* 380:75–79 (1996).

C. J. van Koppen et al., "Activation of a High Affinity $G_i$ Protein–coupled Plasma Membrane Receptor by Sphingosine–1–phosphate," *J. Biol. Chem.* 217(4):2082–2087 (1996).

O. Cuvillier et al., "Suppression of ceramide–mediated programmed cell death by sphingosine–1–phosphate," *Nature* 381:800–803 (1996).

A. Abbas, "Die and Let Live: Eliminating Dangerous Lymphocytes," *Cell* 84:655–657 (1996).

C. Jacob et al., "Heterogeneous effects of IFN–γ in adjuvant arthritis," *J. Immunol.* 142(5):1500–1505 (1989).

K. Goodemote et al., "Involvement of a Pertussis Toxin–sensitiive G Protein in the Mitogenic Signaling Pathways of Sphingosine 1–Phosphate," *J. Biol. Chem.* 270:10272–10277 (1995).

G. H. Fisher et al., "Dominant Interfering Fas Gene Mutations Impair Apoptosis in a Human Autoimmune Lymphoproliferative Syndrome," *Cell* 81:935–946 (1995).

F. Rieux–Laucat et al., "Mutations in Fas Associated with Human Lymphoproliferative Syndrome and Autoimmunity," *Science* 268:1347–1349 (1995).

M. Adachi et al., "Aberrant Transcription Caused by the Insertion of an Early Transposable Element in an Intron of the Fas Antigen Gene of Ipr Mice," *Proc. Natl. Acad. Sci. (USA)* 90:1756–1760 (1993).

B. S. Andrews et al., "Spontaneous Murine Lupus–Like Syndromes: Clinical and Immunopathological Manifestations in Several Strains" *J. Exp. Med.* 148:1198–1215 (1978).

H. Takayama et al., "Cytotoxic T Lymphocytes: The Newly Identified Fas (CD95)–Mediated Killing Mechanism and a Novel Aspect of Their Biological Functions," *Adv. Immunol.* 60:289–321 (1995).

D. W. Nicholson et al., "Identification and Inhibiton of the ICE/CED–3 Protease Necessary for Mammalian Apoptosis," *Nature* 376:37–43 (1995).

(List continued on next page.)

Primary Examiner—Zohreh Fay
Assistant Examiner—Brian-Yong S. Kwon
(74) *Attorney, Agent, or Firm*—Medlen & Carroll, LLP

(57) ABSTRACT

Methods and compositions are described for treating and diagnosing autoimmune diseases, and in particular for treating and detecting rheumatoid arthritis. Treatment is described with a new class of anti-RA drug, namely compounds that inhibit proliferation and induce apoptosis.

5 Claims, 17 Drawing Sheets

OTHER PUBLICATIONS

M. Tewari et al., "Yama/CPP32β, a Mamalian Homolog of CED–3, Is a CrmA–Inhibitable Protease That Cleaves the Death Substrate Poly (ADP–Ribose) Polymerase," *Cell* 81: 801–869 (1995).

A. M. Chinnaiyan et al., "FADD, a Novel Death Domain–Containing Protein, Interacts with the Death Domain of Fas and Inititates Apoptosis," *Cell* 81:505–512 (1995).

S. M. Krane and R.T. Salzman, "Management of Rheumatoid Arthritis and Osteoarthritis; Therapeutic Challenges, Problems and Possibilities," *Am. J. Med.* :75(4B):1–91 (1983).

D. E. Furst, "Are There Differences Among Nonsteroidal Antiinflammatory Drugs; Comparing Acetyated Salicylates, Nonacetylated Salicylates, and Nonacetylated Nonsteroidal Antiinflammatory Drugs," *Arth. & Rheum.* 37(1):1–9 (1994).

B. O. Barger et al., "DR Antigens and Gold Toxicity In White Rheumatoid Arthritis Patients," *Arth. & Rheum.* 27(6):601–605 (Jun. 1984).

H. B. Stein et al., "Adverse Effects of D–Penicillamine in Rheumatoid Arthritis," *Ann. Int. Med.* 92:24–29 (1980).

C. J. Marshall, "Hot Lips and Phosphorylation of Protein Kinases," *Nature* 367:686 (1994).

G. L'Allemain, "Deciphering the Map Kinase Pathway," *Progress in Growth Factor Research* 5:291–334 (1994).

S. A. Susin et al., "The Central Executioner of Apoptosis: Multiple Connections Protease Activation and Mitochondria in Fas/APO/CD95–and Ceramide–Induced Apoptosis," *J. Exp. Med.* 186(1):25–37 (1997).

\* cited by examiner

COMPOSITIONS FOR TREATING AUTOIMMUNE DISEASE

This is a Divisional of application Ser. No. 09/009,906, filed on Jan. 21, 1998, now U.S. Pat. No. 6,098,631 B1.

FIELD OF THE INVENTION

The present invention relates to methods and compositions for treating autoimmune diseases, and in particular for treating rheumatoid arthritis.

BACKGROUND

An "autoimmune" disease is understood to be one where the target of the disease is "self" or "self antigen." There are a number of diseases that are believed to involve T cell immunity directed to self antigens, including (but not limited to) multiple sclerosis (MS), Type I diabetes, and rheumatoid arthritis (RA).

RA is a chronic inflammatory disorder characterized by joint pain. The course of the disease is variable, but can be both debilitating and mutilating. According to conservative estimates approximately 50,000,000 individuals are afflicted with RA worldwide. Those individuals are not only subjected to life-long disability and misery, but as current evidence suggests, their life expectancy is compromised as well. Unfortunately, despite considerable investigative efforts there is no cure for RA.

Established treatments of RA are designed to inhibit either final common pathways of inflammation or immunological mediators. Both approaches are non-specific and, therefore, are associated with severe side effects. Corticosteroids have multiple effects on the immune system and other tissues. Their use is complicated by very high incidence of musculoskeletal, metabolic, neurologic and connective tissue side effects, as well as immunosuppression which may lead to life-threatening infections. For this reason, corticosteroids are usually avoided until all other forms of treatment have failed. See generally, R. Million et al., "Long-Term Study of Management of rheumatoid Arthritis," *Lancet* 1:812 (1984).

Cytotoxic and anti-metabolic drugs, such as methotrexate, azathioprine and cyclophosphamide are non-specifically affecting all rapidly dividing cells and therefore are associated with bone marrow and gastrointestinal toxicity and increased incidence of malignancy. In addition, methotrexate treatment of RA has been reported to induce liver damage and lung disease which may be fatal. See J. A. Engelbrecht et al., "Methotrexate Pneumonitis After Low-Dose Therapy for Rheumatoid Arthritis," *Arthritis and Rheumatism* 26:1275 (1983) and G. W. Cannon et al., "Acute Lung Disease Associated With Low-Dose Pulse Methotrexate Therapy In Patients With Rheumatoid Arthritis," *Arthritis and Rheumatism* 26:1269 (1983).

Most nonsteroidal anti-inflammatory drugs (NSAIDs) currently used are designed to non-specifically inhibit prostaglandin synthesis. NSAIDs currently in use modify or diminish—but do not arrest—the inflammatory response. Aspirin remains the most commonly used NSAID. Aspirin toxicity takes many forms, including hypersensitivity reactions, deafness, gastrointestinal and renal toxicity. See generally Simon and Mills, "Nonsteroidal Antiinflammatory Drugs," *N. Eng. J. Med.* 302:1179 (1980).

Gold compounds and penicillamine have also been used in the treatment of RA. They are both associated with high incidence of bone marrow, renal and mucocutaneous toxicity. Gold treatment, in particular, is associated with nephropathy. W. Katz et al., "Proteinuria in Gold-Treated Rheumatoid Arthritis," *Ann. Int. Med.* 101:176 (1984). Penicillamine, while questionably effective, is toxic even at relatively low doses. See W. F. Kean et al., "The Toxicity Pattern Of D-Penicillamine Therapy," *Arthritis and Rheumatism* 23:158 (1980). These problems have led to almost complete abandonment of these drugs in RA therapy.

Among the experimental therapies, cyclosporin and anti-TNFα antibodies show some promise. However, serious renal toxicity and non-specific immunosuppression limit significantly the utility of cyclosporin. Due to its ubiquitous role in many cellular functions, anti-TNF therapy may not be a safe therapeutic strategy for RA. While preliminary results indicate some promise with the anti-TNF approach, development of lupus-like disease has been noticed in some cases.

Thus, current therapies for RA are associated with high incidence of serious side effects. Furthermore, although some medications may offer symptomatic relief, in many cases, they do not significantly modify the progression of joint destruction. What is needed is an effective therapeutic approach with lower toxicity such that the treatment is better tolerated and more appropriate for the treatment of RA.

SUMMARY OF THE INVENTION

The present invention relates to methods and compositions for treating and diagnosing autoimmune diseases, and in particular for treating and detecting rheumatoid arthritis. The present invention contemplates a new class of anti-RA drug, namely compounds that inhibit proliferation and induce apoptosis. In one embodiment, the present invention contemplates compounds that are inhibitors of the sphingomyelin signal transduction pathway. For example, the present invention contemplates a method of treating a human, comprising: a) providing: i) a human with symptoms of autoimmune disease, and ii) a preparation comprising at least one inhibitor of the sphingomyelin signal transduction pathway, and b) administering said inhibitor to said human under conditions such that said symptoms are reduced.

It is not intended that the present invention be limited to a particular autoimmune disease. In one embodiment, said human has symptoms of rheumatoid arthritis.

It is not intended that the present invention be limited to a particular route of administration. In one embodiment, said administering comprises intravenous injection. In another embodiment, a mixture of inhibitor and DMSO is applied topically at the joints. In a preferred embodiment, said administering comprises intra-articular injection and said preparation further comprises a local anesthetic. Thus, the present invention specifically contemplates mixtures of inhibitors and anesthetics.

It is not intended that the present invention be limited to a particular inhibitor. As described herein, a variety of pathway inhibitors (specific for different steps in the signal transduction pathway) can be used with success, including but not limited to inhibitors of sphingosine kinase and inhibitors of (ii proteins. In this manner, "inhibitors" are defined functionally as a group (rather than structurally). A variety of sphingosine derivatives are known that are herein contemplated as inhibitors, including but not limited to those described in U.S. Pat. Nos. 5,583,160, 5,627,171, 5,466,716, 5,391,800, 5,137,919, 5,151,360, 5,248,824, 5,260,288 and 5,331,014, all of which are hereby incorporated by reference. Preferred derivatives are methylsphingosine, dimethylsphingosine and trimethylsphingosine.

While it is not intended that the present invention be limited by the mechanism by which successful treatment and/or protection against autoimmunity is achieved, it is believed that, although the Fas-mediated apoptosis pathway is intrinsically intact in RA lymphocytes, it is reversibly inhibited by sphingomyelin pathway products. This functional inhibition may be sufficient to allow certain subsets of activated lymphocytes to escape apoptosis and accumulate in the joints, thereby contributing to disease pathogenesis. By introducing agents that block the sphingomyelin pathway, the inhibition of lymphocyte apoptosis is reversed and activated lymphocytes are eliminated in a timely fashion.

The present invention also contemplates methods and reagents for diagnostics. While a variety of cells from patients are comtemplated as suitable for the diagnostic assays of the present invention (e.g. synoviocytes), lymphocytes from patients with rheumatoid arthritis are preferred for assays that detect cells displaying impaired Fas-mediated apoptosis. Lymphocytes from such patients express higher levels of antiapoptotic sphingolipid metabolites (such as sphingosine-1-phosphate) and the present invention contemplates testing for the presence of such metabolites by a variety of means (immunoassays, TLC, HPLC, etc.). In one embodiment, the present invention contemplates a method, comprising: a) providing: i) lymphocytes from a human with symptoms of autoimmune disease, and ii) means for detecting at least one metabolite of the sphingomyelin signal transduction pathway: and b) testing said lymphocytes with said means for detecting under conditions such that elevated levels (i.e., elevated relative to lymphocytes from controls) of said metabolite are detected. In one embodiment, said means for detecting is an antibody.

Definitions

The term "apoptosis inducing agent" refers to any compound or molecule which is capable of causing (directly or indirectly) apoptosis, including but not limited to, inhibitors of the sphingomyelin signal transduction pathway. The present invention contemplates administration of apoptosis inducing agents to autoimmune patients.

The term "sphingomyelin pathway inhibitor" is used herein to refer to compounds that inhibit downstream events in the sphingomyelin pathway, including but not limited to, inhibitors of sphingosine kinase and Gi proteins inhibitors. Such inhibitors are contemplated to reverse the resistance to apoptosis in RA lymphocytes. Thus, such inhibitors (and apoptosis inducing agents generally) are defined functionally. This function can be readily assessed by using the in vitro assays of the present invention (described below).

The term "subject" refers to both humans and animals.

The term "receptors" refers to structures expressed by cells and which recognize binding molecules (e.g., ligands).

The term "antagonist" refers to molecules or compounds which inhibit the action of a "native" or "natural" compound. Antagonists may or may not be homologous to these natural compounds in respect to conformation, charge or other characteristics. Thus, antagonists may be recognized by the same or different receptors that are recognized by the natural compound. Thus, a kinase inhibitor is a kinase antagonist.

The term "symptoms of RA" is intended to encompass any and all symptoms. Where a symptom is said to be "reduced" it is indicated that the degree of such symptom (such as the degree of joint pain or the amount of inflammatory cells in the joints) is diminished. The present invention is not limited to any particular quantitative level. Most importantly, the present invention is not limited to the complete elimination of symptoms.

The term "drug" as used herein, refers to any medicinal substance used in humans or other animals. Encompassed within this definition are compound analogs, naturally occurring, synthetic and recombinant pharmaceuticals.

DESCRIPTION OF THE INVENTION

Figure 1:
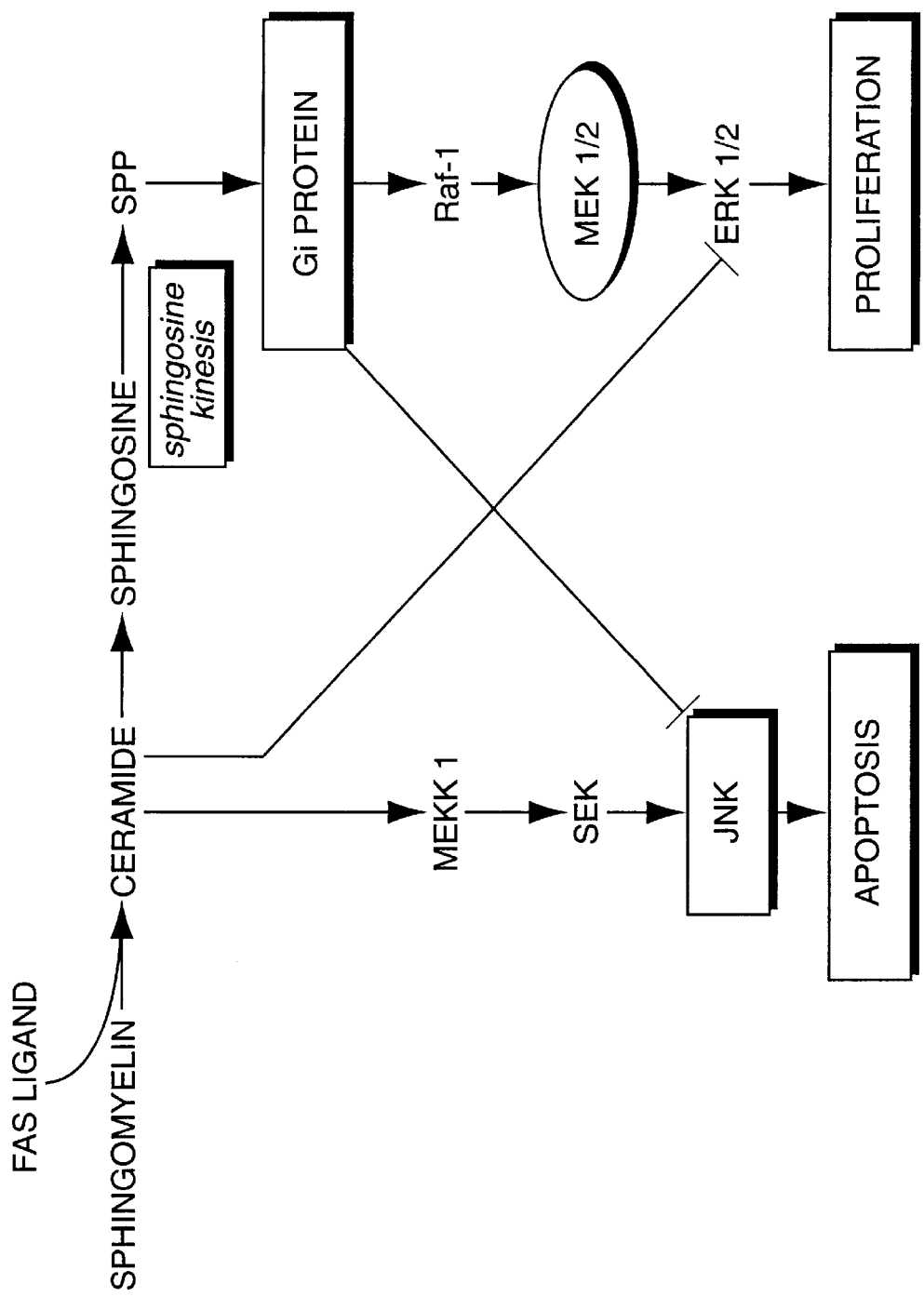
FIG. 1 is a schematic showing various targets of the sphingomyelin pathway for RA therapy according to the teachings of the present invention.

The present invention relates to methods and compositions for treating autoimmune diseases, and in particular for treating rheumatoid arthritis with sphingomyelin pathway inhibitors. The description of the invention that follows discusses I) Fas-mediated Apoptosis, II) Apoptosis And The Immune System, III) Reversing The Resistance to Apoptosis As A Treatment Of Autoimmune Disease. IV) Formulation of Inhibitors of the Sphingomyelin Pathway, and V) Delivery of Formulations and Intra-articular Injections.

I. Fas-Mediated Apoptosis

Homeostasis of mammalian tissues is controlled not only by proliferation and differentiation of cells, but also by cell death. There are two death processes, apoptosis and necrosis. The death of cells during embryogenesis, metamorphosis, endocrine-dependent tissue atrophy, and normal tissue turnover is called programmed cell death. Most of the programmed cell death which occurs during mammalian development proceeds by apoptosis.

Apoptosis can be distinguished morphologically and biochemically from necrosis. Necrosis occurs during pathological cell death as a result of injury, complement attack, severe hypoxia, hyperthermia, lytic viral infection, and exposure to a variety of toxins. Apoptosis is accompanied by condensation and segmentation of nuclei, loss of plasma membrane microvilli, and extensive degradation of the chromosomal DNA into nucleosome units.

It is believed that the apoptotic signal is induced by the binding, of the Fas ligand to Fas. See generally, S. Nagata. "Fas and Fas Ligand: A Death Factor and Its Receptor." *Advances in Immunology* 57:129 (1994). The cytoplasmic domain of Fas consists of 145 amino acids. About 70 amino acids in this region have significant similarity with a part of the cytoplasmic region of the type I (but not type II) TNF receptor. Indeed, analyses of point mutations in the Fas protein in this conserved region have shown that the domain is essential for the function of Fas.

The Fas ligand has been identified, isolated, and cloned. The amino acid sequence deduced from the nucleotide sequence of the cDNA indicates that the Fas ligand is a TNF-related type II membrane protein. However, despite the high similarity between Fas ligand and TNF (about 30% identical at the amino acid sequence level). Fas ligand does not bind to the TNF receptor.

The tissue distribution of Fas mRNA in the mouse has been examined. Fas mRNA can be detected abundantly in the thymus, heart, liver, and ovary of 8-week old mice, but not in the brain, bone marrow, and spleen. Fas is expressed in almost all populations of thymocytes. This, wide distribution of Fas is in sharp contrast to the tissue restrictive expression of Fas ligand; Fas ligand is found on the Sertoli cells of the testis, on the corneal epithelium, iris and retina, and on activated T lymphocytes.

The activation of Fas is caused by aggregation mediated by the Fas ligand (or other agonist, such as antibodies). The signal is thought to be transduced by clustering of the intracellular domain. The downstream elements of the apoptosis process are thought to be affected by the sphingomyelin signal transduction pathway. See generally,. R. N. Kolesnick et al., "The Sphingomyelin Signal Transduction Pathway Mediates Apoptosis For Tumor Necrosis Factor, Fas, and Ionizing Radiation," *Biochem. Cell Biol.* 72:471 (1994). This pathway is initiated by enzymatic hydrolysis of the phosphodiester bond of sphingomyelin by a specific sphingomyelin-directed phospholipase C ("sphingomyelinase"), generating ceramide and phosphocholine.

Ceramide serves as the second messenger of the pathway, initiating signaling for several biological agents. Ultimately, ceramide activates the death signaling pathway in a Jun kinase (JNK)-mediated pathway. See M. Verheij et al., "Requirement for ceramide-initiated SAPK/JNK signaling in stress-induced apoptosis," *Nature* 380:75 (1996).

Ceramide, however, can also be metabolized to sphingosine and sphingosine-1-phosphate (SPP) by the action of ceramidase and sphingosine kinase, respectively. See generally C. J. van Koppen et al., "Activation of a High Affinity $G_i$ Protein-coupled Plasma Membrane Receptor by Sphingosine-1-phosphate," *J. Biol. Chem.* 217:2082 (1996). SPP has been shown to be involved in stimulating DNA synthesis and cell division, i.e., proliferation. Importantly, SPP has been recently shown to inhibit Fas-mediated cell death. See O. Cuvillier et al., "Suppression of ceramide-mediated Programmed Cell Death By Sphingosine-1-phosphate," *Nature* 381:800 (199).

II. Apoptosis and the Immune System

The principal physiologic function of the immune system is the elimination of infectious organisms. The effector mechanisms that are responsible for protective immunity are also capable of injuring host tissues. In some situations, specific immune responses have little or no protective value, and the harmful consequences become dominant. The best example of this is autoimmune disease caused by pathologic immune responses against self-antigens.

The immune system has evolved multiple mechanisms for controlling potentially harmful reactions. Failure of these mechanisms may lead to tissue injury and disease. Potentially harmful immune reactions may be prevented either by functionally inactivating or killing the responding lymphocytes. The primary cytolytic mechanism involved in controlling lymphocyte responses is the Fas-mediated apoptotic pathway discussed above. In this manner, the immune system actively eliminates potentially harmful cells so that the host may survive. See A. Abbas, "Die and Let Live: Eliminating Dangerous Lymphocytes." *Cell* 84:655 (1996).

The mechanism by which Fas-Fas Ligand interactions maintain immunological tolerance to self-antigens is yet to be completely understood. It is believed that repeated stimulation of antigen cause T cells to express high levels of Fas and Fas Ligand, thereby killing either themselves or one another. Such a homeostatic mechanism may limit the size of lymphocyte clones responding to foreign antigens. The same mechanism may be triggered by abundant and disseminated self-antigens, which are able to interact repeatedly with specific T cells.

Abnormalities in Fas-mediated cell death pathways may result in autoimmunity even in situations in which Fas and Fas Ligand are themselves normal, for example, where apoptosis is inhibited and a proliferation pathway is stimulated, activated lymphocytes may escape elimination and cause disease. The present invention contemplates reversing the resistance to apoptosis by inhibiting downstream events of the sphingomyelin pathway. In this manner, activated lymphocytes go through the apoptosis pathway and are eliminated. It is believed that such treatment of RA patients will reduce the symptoms that are characteristic of RA.

III. Reversing the Resistance to Apoptosis as a Treatment of Autoimmune Disease

It is not intended that the present invention be limited to particular points in the sphingomyelin pathway or particular inhibitors of the sphingomyelin pathway. As noted above, SPP has been recently shown to inhibit the Fas-mediated cell death pathway. While, the present invention contemplates inhibiting SPP, thereby reversing the inhibition of Fas-mediated apoptosis, the present invention also contemplates inhibiting the sphingomyelin pathway at other points. FIG. 1 is a schematic showing the broad nature of the targets contemplated for therapeutic intervention in RA.

As shown in FIG. 1 (and discussed above), following Fas ligation, sphingomyelin is converted to ceramide through the activation of acid sphingomyelinase. Ceramide activates the death signaling pathway in a Jun kinase (JNK)-mediated pathway. Through its inhibitory effect on ERK 1/2, ceramide can also block proliferation, thus shifting the balance further toward apoptosis.

Since increased levels of ceramide may promote programmed cell death, in one embodiment, the present invention contemplates treatment of RA patients with inhibitors of ceramide catabolism. It is not intended that the present invention be limited by the nature of the inhibitor. In one embodiment, the present invention contemplates inhibiting ceramide catabolism by inhibiting its conversion to free sphingosine by ceramidase [e.g., by using N-oleoylethanolamine, (1S,2R)-D-erythro-2-(N-myristoylamino)-phenyl-1-propanol ("D-MAPP") or other suitable inhibitor]. In another embodiment, the present invention contemplates inhibiting ceramide catabolism by inhibiting metabolism to glucosylceramide by glucosylceramide synthase [e.g., by using D-threo-1-phenyl-2-decanoylamino-3-morpholino-1-propanol ("PDMP") and newer homologues or by using N-butyldeoxynojirimycin or other suitable inhibitors]. In yet another embodiment, the present invention contemplates inhibiting ceramide catabolism by inhibiting metabolism to sphingomyelin by sphingomyelin synthase or by inhibiting metabolism to ceramide-1-phosphate by ceramide kinase. In still another embodiment, the present invention contemplates inhibiting ceramide catabolism by inhibiting metabolism to 1-O-acylceramide by ceramide transacylase (e.g. by using D- and L-erythro enantiomers of PDMP and related homologues).

On the other hand, as discussed above. SPP has an antagonistic effect to that of ceramide. It is produced from sphingosine by the activity of sphingosine kinase. It has a dual, Gi-protein-dependent, anti-apoptotic effect. It blocks JNK activation on the one hand, and leads to ERK 1/2 activation on the other. Thus, the net effect of SPP is inhibition of ceramide-mediated cell death.

While it is not intended that the present invention be limited to a precise understanding of the mechanism, it is believed that resistance to Fas-mediated cell death in RA is due to a shift in the ceramide/SPP rheostat. Suppressing the pathway (e.g. by suppressing SPP synthesis with a sphingosine kinase inhibitor, or blocking its Gi-mediated effects) can both restore the susceptibility of RA lymphocytes to killing by Fas ligation. Accordingly, targets for therapeutic intervention in RA include (but are not limited to) inhibition of sphingosine kinase, inhibition of Gi proteins, inhibition of MEK1, activation of JNK, or a combination of two or more of those modalities.

In one embodiment, the present invention contemplates treating RA patients with compounds that inhibit sphingosine-phosphate formation. While inhibition of sphingosine kinase (e.g., with sphingosine derivatives) has been discussed, other approaches to inhibiting sphingosine phosphate formation are contemplated, including inhibiting (1) synthesis of long chain bases (e.g. by use of β-chloroalanine or L-cycloserine or other suitable inhibitor), (2) inhibition of acylation of long chain bases, a critical step in eventual sphingosine formation (e.g. using fumonisin B1 or other suitable inhibitor), and (3) stimulation of sphingosine-1-phosphate phosphatase or lyase.

IV. Formulation of Inhibitors of the Sphingomyelin Pathway

The present invention contemplates preparations comprising inhibitors of the sphingomyelin signal transduction pathway. Such formulations can be prepared either as liquid solutions or suspensions, or in solid forms. Formulations may include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%.

The compositions are also prepared as injectables, either as liquid solutions or suspensions; solid forms suitable for solution in, or suspension in, liquid prior to injection may also be prepared. For intra-articular injections (see below), the present invention contemplates formulations comprising one or more inhibitors of the sphingomyeline pathway along with one or more local anesthetic. It is not intended that the present invention be limited to particular anesthetics. A variety are contemplated including but not limited to procaine or lidocaine. When injecting a bursa, tendon sheath, or periarticular region, such a mixture will give immediate relief (due to the anesthetic) followed by more lasting relief (due to the inhibitor).

Where mixtures with local anesthetics are not desired, a topical anesthetic prior to injection may be used. Such topical anesthetics include but are not limited to ethyl chloride spray on the skin over the joint to be injected. Alternatively, a local anesthetic may be given first, followed by administration of one or more of the above-described inhibitors.

V. Delivery of Formulations and Intra-articular Injections

It is not intended that the present invention be limited to the particular route of administration. The sphingomyelin pathway inhibitors can be given orally or injected (including but not limited to intravenous injection). The present invention specifically contemplates intra-articular injections in RA patients.

To perform an arthrocentesis, the specific area of the joint to be injected is palpated and is then marked, e.g., with firm pressure by a ballpoint pen that has the inked portion retracted. This will leave an impression that will last 10 to 30 minutes. (The ballpoint pen technique can also be used with soft tissue injection.) The area to be aspirated and/or injected should be carefully cleansed with a good antiseptic, such as one of the iodinated compounds. Then the needle can be inserted through the ballpoint pen impression.

Helpful equipment includes the following items: alcohol sponges; iodinated solution and surgical soap; gauze dressings (2×2); sterile disposable 3-, 10- and 20-ml syringes; 18- and 20-gauge, 1½-inch needles; 20-gauge spinal needles; 25-gauge, ⅝-inch needles; plain test tubes; heparinized tubes; clean microscope slides and coverslips; heparin to add to heparinized tubes if a large amount of inflammatory fluid is to be placed in the tube; fingernail polish to seal wet preparation; chocolate agar plates or Thayer-Martin medium; tryptic soy broth for most bacteria; anaerobic transport medium (replace periodically to keep culture media from becoming outdated); tubes with fluoride for glucose; plastic adhesive bandages; ethyl chloride; hemostat; tourniquet for drawing of simultaneous blood samples; and 1 percent lidocaine.

Knee

The knee is the easiest joint to inject. The patient should be in a supine position with the knee fully extended. The puncture mark is made just posterior to the medial portion of the patella, and an 18- to 20-gauge, 1½-inch needle directed slightly posteriorly and slightly inferiorly. The joint space should be entered readily. On occasion thickened synovium or villous projections may occlude the opening of the needle, and it may be necessary to rotate the needle to facilitate aspiration of the knee when using the medial approach. An infrapatellar plica, a vestigal structure that is also called the ligamentum mucosum, may prevent adequate aspiration of the knee when the medial approach is used. However, the plica should not adversely affect injections or aspirations from the lateral aspect.

Shoulder

Injections in the shoulder are most easily accomplished with the patient sitting and the shoulder externally rotated.

A mark is made just medial to the head of the humerus and slightly inferiorly and laterally to the coracoid process. A 20- to 22-gauge, 1½-inch needle is directed posteriorly and slightly superiorly and laterally. One should be able to feel the needle enter the joint space. If bone is hit, the operator should pull back and redirect the needle at a slightly different angle.

The acromioclavicular joint mast be palpated as a groove at the lateral end of the clavicle just medial to the shoulder. A mark is made, and a 22- to 25-gauge. ⅝ to 1-inch needle is carefully directed inferiorly. Rarely is synovial fluid obtained.

The sternoclavicular joint is most easily entered from a point directly anterior to the joint. Caution is necessary to avoid a pneumotharax. The space is fibrocartilaginous, and rarely can fluid be aspirated.

Ankle Joint

For injections of the inhibitors of the present invention in the ankle joints, the patient should be supine and the leg-foot angle at 90 degrees. A mark is made just medical to the tibialis anterior tendon and lateral to the medial malleolus. A 2- to 22-gauge, 1½-inch needle is directed posteriorly and should enter the joint space easily without striking bone.

Subtalar Ankle Joint

Again, the patient is supine and the leg-foot angle at 90 degrees. A mark is made just inferior to the tip of the lateral mallcolus. A 20- to 22-gauge, 1½-inch needle is directed perpendicular to the mark. With this joint the needle may not enter the first time, and another attempt or two may be necessary. Because of this and the associated pain, local anesthesia may be helpful.

Wrist

This is a complex joint, but fortunately most of the intercarpal spaces communicate. A mark is made just distal to the radius and just ulnar to the so-called anatomic snuff box. Usually a 24- to 26-gauge, ⅝ to 1-inch needle is adequate, and the injection is made perpendicular to the mark. If bone is hit, the needle should be pulled back and slightly redirected toward the thumb.

First Carpometacarpal Joint

Degenerative arthritis often involves this joint. Frequently the joint space is quite narrowed, and injections may be difficult and painful. A few simple maneuvers may make the injection fairly easy, however. The thumb is flexed across the palm toward the tip of the fifth finger. A mark is made at the base of the first metacarpal bone away from the border of the snuff box. A 22- to 26-gauge, ⅝ to 1-inch needle is inserted at the mark and directed toward the proximal end of the fourth metacarpal. This approach avoids hitting the radial artery.

Metacarpophalalangeal Joints and Finger Interphalangral Joints

Synovitis in these joints usually causes the synovium to bulge dorsally, and a 24- to 26-gauge. ½ to ⅝-inch needle can be inserted on the either side just under the extensor tendon mechanism. It is not necessary for the needle to be interposed between the articular surfaces. Some prefer having the fingers slightly flexed when injecting the metacarpophalangeal joints. It is unusual to obtain synovial fluid. When injecting, a mix of the inhibitors of the present invention with a small amount of local anesthetic is preferred.

Metatarsophalangeal Joints and Toe Interphalangeal Joints

The techniques are quite similar to those of the metacapophalangeal and finger interphalangeal joints, but many prefer to inject more dorsally and laterally to the extensor tendons. Marking the area(s) to be injected is helpful as is gentle traction on the toe of each joint that is injected.

Elbow

A technique preferred by many is to have the elbow flexed at 90 degrees. The joint capsule will bulge if there is inflammation. A mark is made just below the lateral epicondyle of the humerus. A 22-gauge, 1 to 1½-inch is inserted at the mark and directed parallel to the shaft of the radius or directed perpendicular to the skin.

Hip

This is a very difficult joint to inject even when using a fluoroscope as a guide. Rarely is the physician quite sure that the joint has been entered; synovial fluid is rarely obtained. Two approaches can be used, anterior or lateral. A 20-gauge, 3½-inch spinal needle should be used for both approaches.

For the anterior approach, the patient is supine and the extremity fully extended and externally rotated. A mark should be made about 2 to 3 cm below the anterior superior iliac spine and 2 to 3 cm lateral to the femoral pulse. The needle is inserted at a 60 degree angle to the skin and directed posteriorly and medially until bone is hit. The needle is withdrawn slightly, and possibly a drop or two of synovial fluid can be obtained, indicating entry into the joint space.

Many prefer the lateral approach because the needle can "follow" the femoral neck into the joint. The patient is supine, and the hips should be internally rotated the knees apart and toes touching. A mark is made just anterior to the greater trochanter, and the needle is inserted and directed medially and sightly cephalad toward a point slightly below the middle of the inguinal ligament. One may feel the tip of the needle slide into the joint.

Temporomandibular Joint

For injections, the tempormandibular joint is palpated as a depression just below the zygomatic arch and 1 to 2 cm anterior to the tragus. The depression is more easily palpated by having the patient open and close the mouth. A mark is made and, with the patient's mouth open, a 22-gauge, ½ to 1-inch needle is inserted perpendicular to the skin and directed slightly posteriorly and superiorly.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L. (liters); ml (milliliters); $\mu$l (microliters); cm (centimeters); mm (millimeters); $\mu$m (micrometers); nm (nanometers): ° C. (degrees Centigrade); DMS (N,N-dimethylsphingosine); ERK [Extra-cellularly Regulated Kinase (ERK1 for the $p44^{mapk}$; ERK2 for the $p42^{mapk}$; ERK3 for the $p63^{mapk}$)]; MAPK (Mitogen-Activated Protein Kinase) (see generally, U.S. Pat. Nos. 5,663,313 and 5,663,314, both of which are hereby incorporated by reference); MAPKK (MAP kinase kinase); MEK (Mitogenically Extraregulated Kinase); MEKK (ME kinase kinase); z-VAD-fmk [N-benzyloxycarbonyl-Val-Ala-Asp (O-methyl)-fluromethylketone].

In some of the examples below, the TUNEL assay was used. TdT-mediated dUTP-biotin nick end-labeling (TUNEL) assay was performed as described [see (Gorczyca, W, et al. *Leukemia* 7, 659–70 (1993)]. Briefly, cells were fixed in 1% buffered formaldehyde (pH 7.4) for 15 min on ice, washed in phosphate-buffered saline (PBS) and stored at 4° C. in 70% ethanol. Subsequently, cells were resuspended in 50 $\mu$l of a solution containing: 5 unites of terminal deoxynucleotidyl transferase (Boehringer Mannheim, Indianapolis, Ind.), 2.5 mM $CoCl_2$, 0.2 M potassium cacodylate, 25 mM Tris-HCl, 0.25 mg/ml bovine serum albumin, 0.5 nmoles biotin-16-dUTP (Boehringer Mannheim Biochemicals, Indianapolis, Ind.). Cells were incubated in this solution at 37° C. for 30 min, then rinsed in PBS and resuspended in 100 μl of staining solution, containing 2.5 μg/ml fluorescinated avidin, 4×concentrated saline sodium citrate buffer, 0.1% Triton X-100, and 5% (w/v) non-fat dry milk. Cells were incubated in this solution for 30 min at room temperature in the dark. Cells were then rinsed in PBS containing 0.1% Triton X-100 and resuspended in 1 ml in PBS containing 5 μg/ml propidium iodide and 0.1% RNase (Sigma). Green (b-dUTP) and red (DNA) fluorescence of individual cells were measured with an EPICS Elite Flow Cytometer (Coulter, Hialeah. Fla., USA).

In some examples below, methods were used to determine DNA fragmentation. One method involves the demonstration of DNA laddering on agarose gels. Briefly, cells were lysed in TE buffer containing 0.2% Triton X-100, pH 8. Fragmented DNA was separated from intact chromatin by microfuging for 20 min, 14,000 rmp in 4° C. The resulting supernatant was treated with 1 mg/ml of proteinase K at 37° C. overnight, then extracted with phenol/chloroform/isoamyl alcohol (25:24:1) three times. DNA was precipitated by addition of three volumes of absolute ethanol, in the presence of 0.3 M sodium acetate, pH 5.2, and incubated overnight at −20° C. and then pelleted by centrifugation at 14,000 rpm at 4° C. for 20 mil. The pellet was washed twice with 75% ethanol and dissolved in 30 μl of TE containing 10 μg/mil of RNase overnight at 37° C. DNA samples were separated by electrophoresis on 1.8% agarose gel in the presence of ethidium bromide.

In some examples below, Western blots were performed. For Western blot analysis, 5×10$^6$ cells were washed and suspended in 100 μl of lysis buffer [1% sodium dodecyl sulfate (SDS), 1 mM sodium vanadate, 10 mM Tris (pH 7.6)], and boiled for 5 min. After micro-centrifugation at 14,000 rpm, for 10 min, supernatants (cell lysates) were recovered. The protein concentration of the lysates was determined with bicinchoninic acid (BCA) protein assay reagent (Pierce). For CPP32 immunoblots, cell lysates (10–20 μg of protein per lane) were separated on 15% SDS-polyacrylamide gels under reducing conditions, transferred to polyvinylidene difluoride (PVDF) membranes (Millipore), and probed with mouse monoclonal anti-CPP32 (clone #19, IgG2a, from Signal Transduction Labs, Lexington, Ky.) followed by sheep F(ab')2 fragment horseradish peroxidase-conjugated, anti-mouse Ig (Amersham). For PARP immunoblots, cell lysates (10 μg of protein per lane) were separated on 7.5% SDS-polyacrylamide gels, transferred to PVDF membrane, and probed with monoclonal mouse anti-human PARP antibody C2.10 (IgG1, Enzyme Systems Products Dublin, Calif.). Antibody binding was detected with an ECL detection system (Amersham).

Example 1

In this example, the susceptibility of lymphocytes to cell death is examined. As noted above, it is believed that prevention of immune-mediated self injury requires prompt elimination of activated lymphocytes at the end of an immune response. In this example, the resistance of T cells of RA patients to anti-Fas antibody-induced death is demonstrated. Briefly, PHA T cell lymphoblasts from 6 normal controls and 6 RA patients were established by stimulating peripheral blood mononuclear cells with 0.5 μg/ml PHA for 3 days, followed by expansion in 20 U/ml of recombinant human IL-2 (Collaborative Biomedical Products, Bedford, Mass.). Day-10 T cell lymphoblasts were incubated with 125 ng/ml of the agonist anti-Fas monoclonal antibody CH-11 (the antibody was immobilized and 1×10$^5$ cells per well were used). In all experiments, control mouse monoclonal IgM antibody (TEPC-183, from Sigma) was used in equivalent concentrations. Cell death was determined at different time points, using a commercial MTS kit (Promega, Madison. Wis.). Microplate wells were read by ELISA plate reader at 490 nm.

Figure 2A:
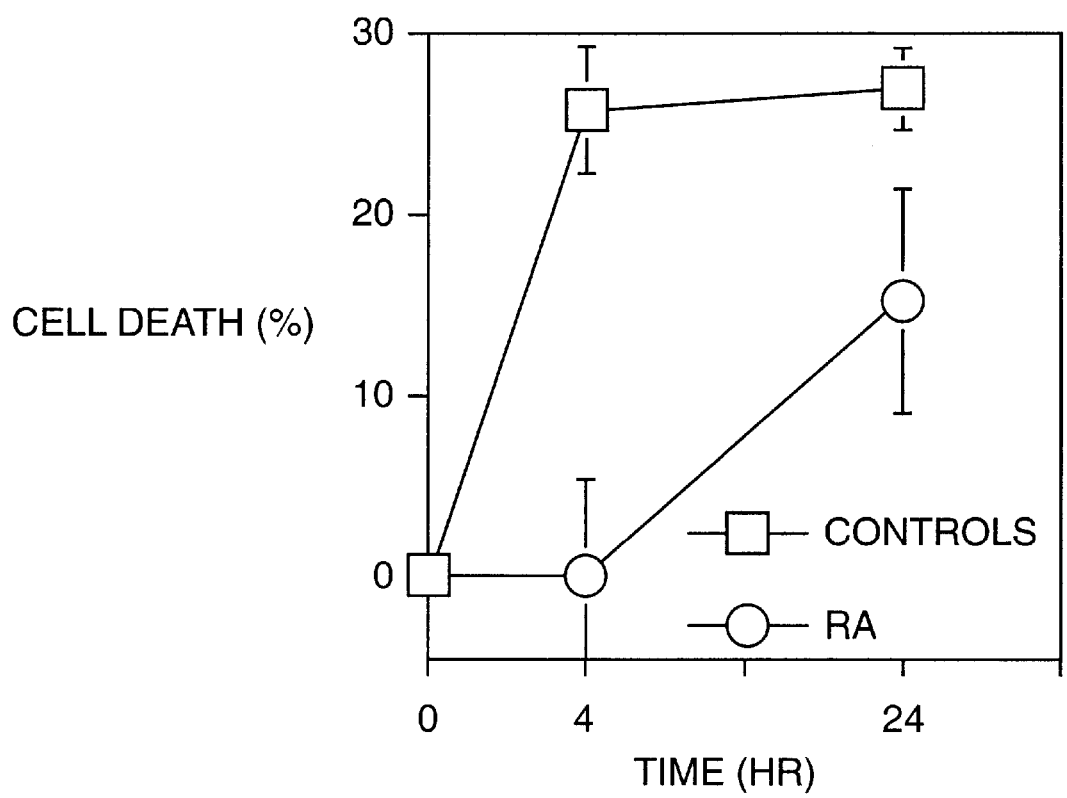
FIG. 2A is a graph showing the susceptibility of normal and RA T cells to apoptosis.

FIG. 2A shows that activated lymphocytes of the T-cell lineage from normal individuals (open squares) die rapidly after exposure to the agonist anti-Fas antibody CH-11. In contrast, T lymphocytes of RA patients (open circles) show complete resistance to killing up to 4 hours following ligation. Some susceptibility, however, can be seen in these cells at the 24 hour time point. Thus, at the critical early period, RA cells are resistant to killing by Fas-ligation.

Figure 2B:
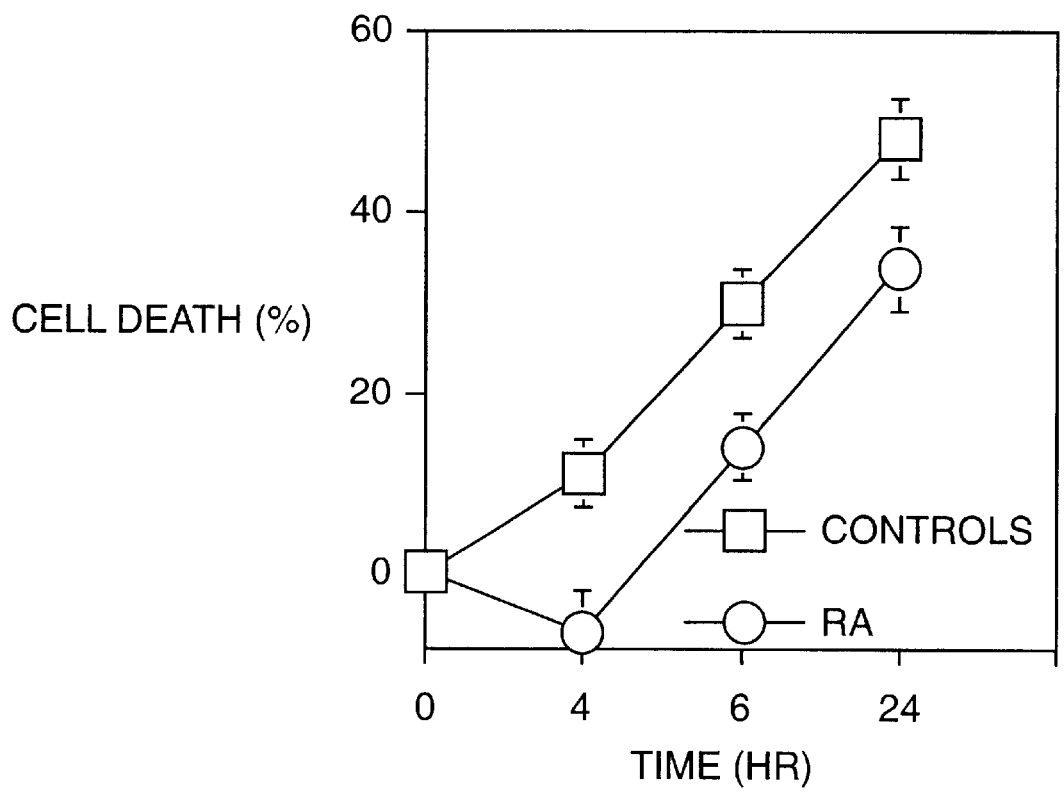
FIG. 2B is a graph showing the susceptibility of EBV-transformed, normal and RA B cells to apoptosis.

FIG. 2B shows that activated lymphocytes of the B-cell lineage (i.e. EBV transformed B cell lines) from 4 normal individuals (open squares) also die rapidly. However, EBV transformed B cell lines from 5 RA individuals (open circles) show resistance to anti-Fas antibody-induced death (soluble anti-Fas antibody was used and percent cell death determined as above).

Figure 2C:
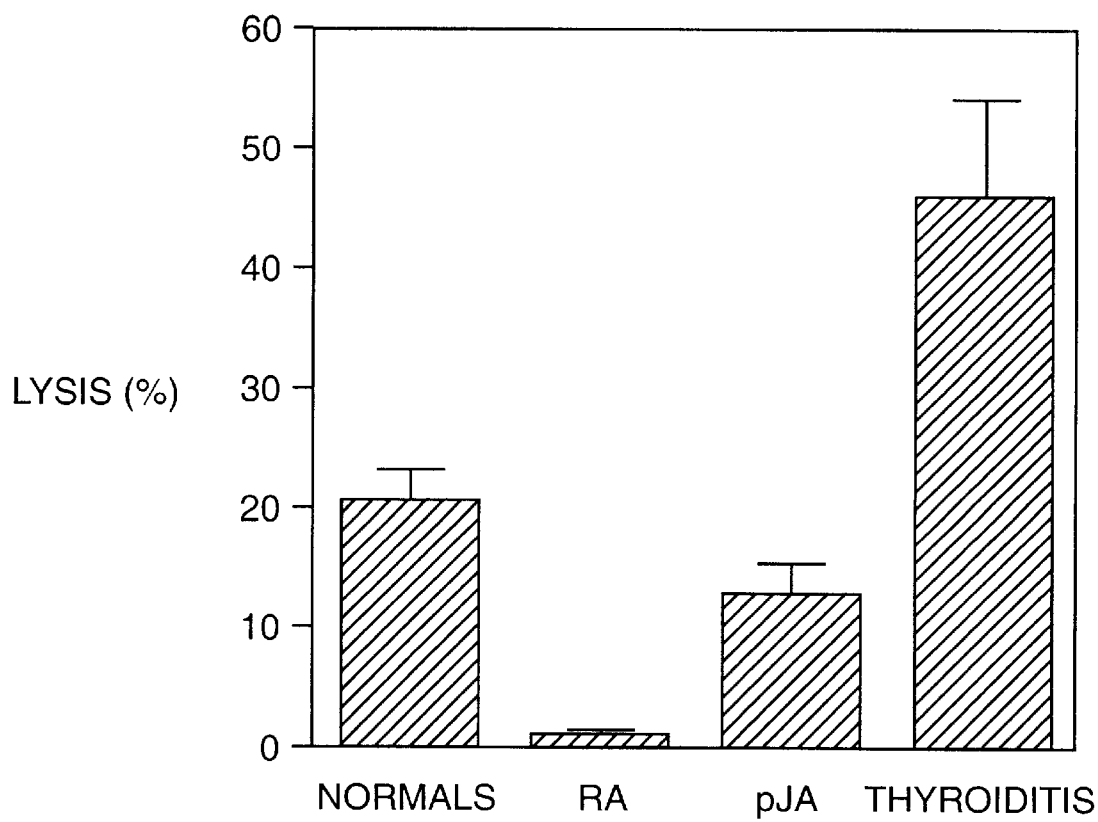
FIG. 2C is a graph showing the susceptibility of cells to T cell-mediated cytolysis.

Fas-mediated cell death in-vivo is thought to be triggered, primarily, by cytotoxic T cells. Lymphocytes expressing the Vγ9/Vδ2 (Vgamma9/Vdelta2) T cell receptor have previously been found to display potent MHC-unrestricted cytolytic activity against a wide variety of targets and have been found in large numbers in the synovial fluid and peripheral blood of RA patients. The present inventors have found that RA and control B lymphoblastoid targets were equally capable of forming cell conjugates with Vγ9/Vδ2 T-cells (data not shown). However, susceptibility to cytolysis is markedly different between the two groups when determined using standard 4 hour $^{51}$Cr release assays. FIG. 2C is a bar graph showing the susceptibility to cytolysis by Vγ9/Vδ2 T cell clones determined in EBV transformed lines from 23 normal controls, 18 patients with RA, 6 patients with pauciarticular-onset juvenile arthritis ("pJA"), and 3 patients with autoimmune thyroiditis. Lymphoblastoid target lines from all 23 normal controls tested were efficiently killed by Vγ9/Vδ2 clones, while none of the lines from 18 RA patients were susceptible. This resistance was disease-specific, since lines from 5 of 6 patients with another form of autoimmune arthritis (pauciarticular-onset juvenile arthritis), as well as lines from three patients with autoimmune thyroiditis, were all susceptible.

Example 2

Figure 3A:
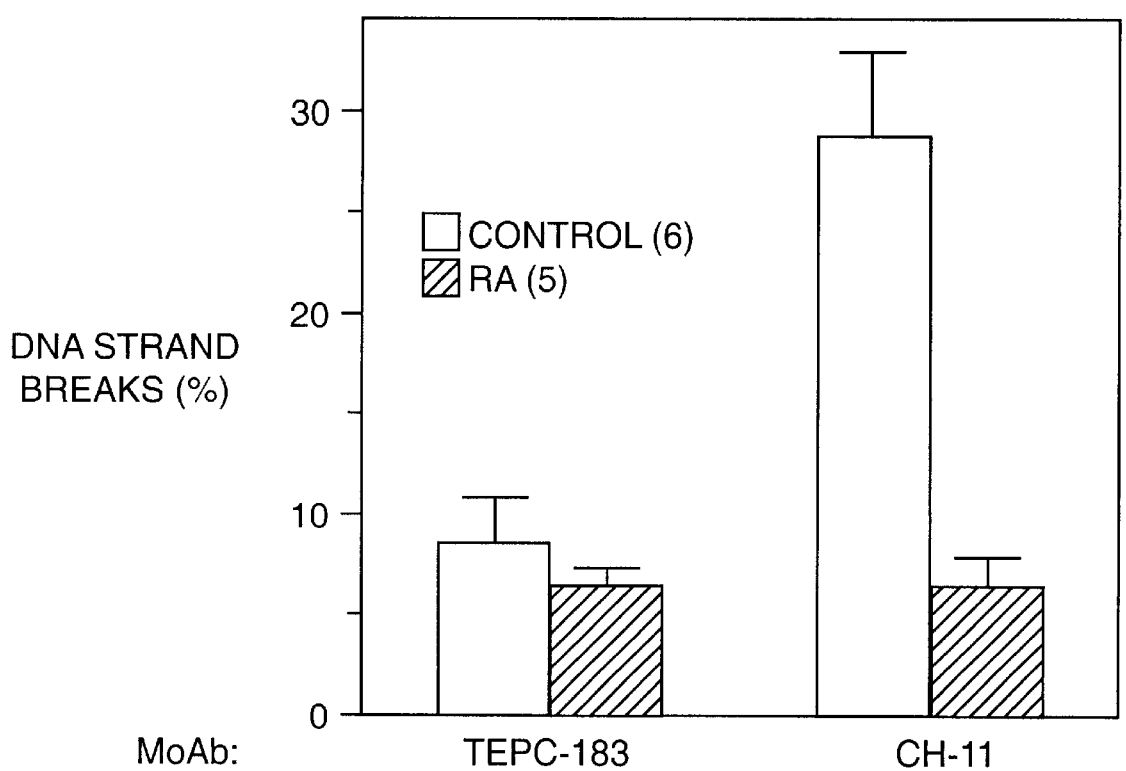
FIG. 3A is a graph showing anti-Fas antibody-mediated DNA fragmentation by the TUNEL assay in EBV transformed B cell lines from normal controls and RA patients.
Figure 3B:
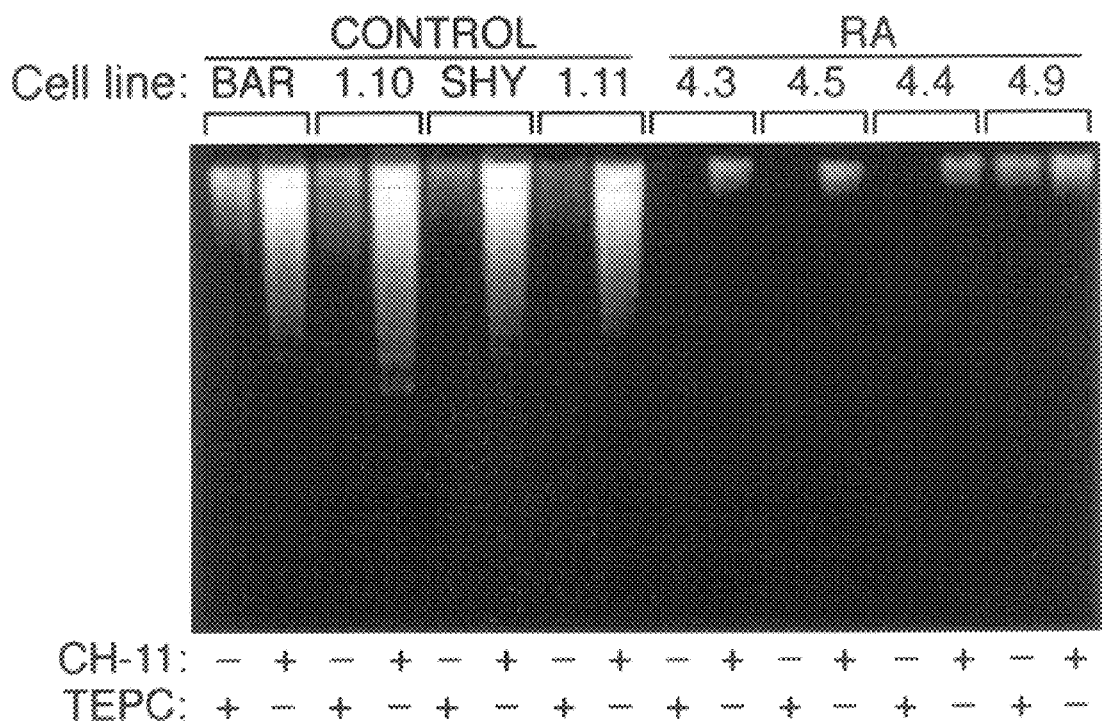
FIG. 3B is a photograph of an agarose electrophoresis gel showing anti-Fas antibody-mediated DNA fragmentation in EBV transformed B cell lines from 4 normal controls and 4 RA patients.

The experiments in this example show that resistance of RA lymphocytes to killing is due to failed apoptosis. Briefly, anti-Fas antibody-mediated DNA fragmentation by the TUNEL assay was performed in EBV transformed B cell lines from 6 normal controls (FIG. 3A, open bars) and 5 RA patients (FIG. 3B, dashed bars). Cells were incubated with either the agonist anti-Fas antibody, CH-11, or with isotype-matched control antibody, TEPC-183 before analysis of DNA fragmentation. Fas ligation resulted in DNA fragmentation in control lymphocytes, but not in RA lymphocytes.

Anti-Fas antibody-mediated DNA fragmentation was also analyzed in EBV transformed B cell lines from 4 normal controls (FIG. 3B, left) and 4 RA patients (FIG. 3B, right) by agarose electrophoresis. Again, cells were incubated with either the agonist anti-Fas antibody, CH-11, or with isotype-matched control antibody, TEPC-183 before analysis of DNA fragmentation. Again, Fas ligation resulted in DNA fragmentation of control cells, but not RA lymphocytes.

Figure 3C:
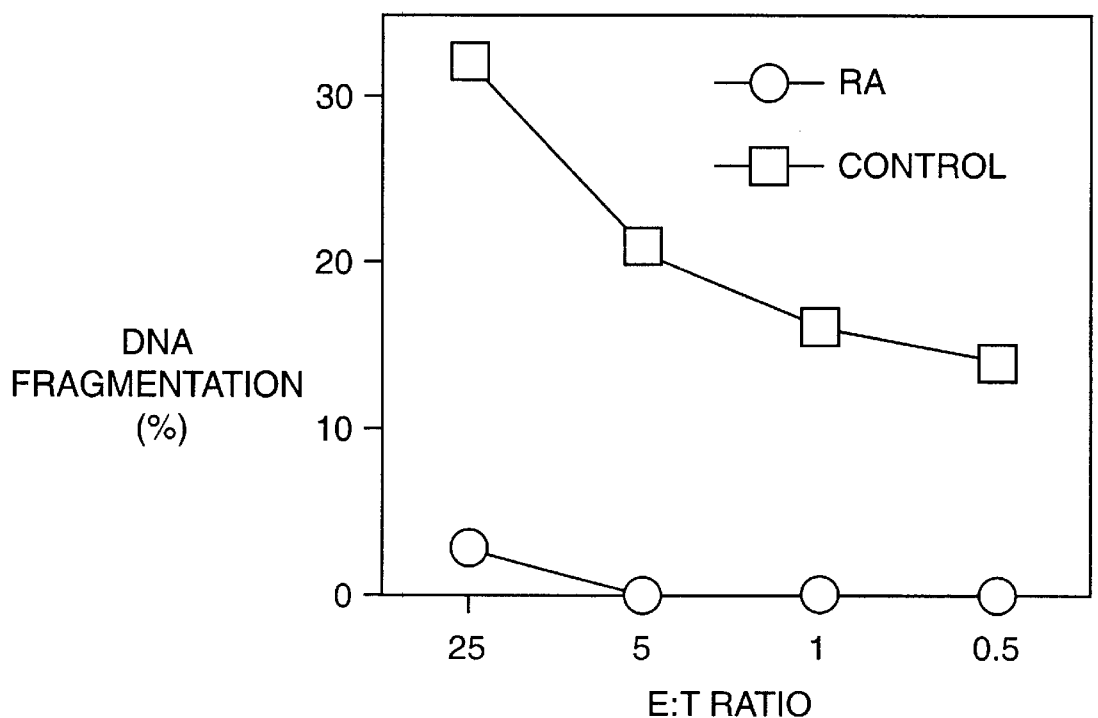
FIG. 3C is a graph showing DNA fragmentation by the JAM assay in EBV transformed lines from a normal control and an RA patient.

DNA fragmentation by the JAM assay was also performed in EBV transformed lines (FIG. 3C) from a normal control (□) and an RA patient (○), subjected to γδ T cell-mediated killing. Lack of DNA fragmentation in RA target cells was also observed during Vγ9/Vδ2 T-cell-mediated killing.

While the present invention is not limited to any theory, it is believed that RA lymphocytes are not innately resistant to programmed cell death, as they display some susceptibility to Fas-mediated cell death at the late time points, and more importantly, T-cells from both patients and controls are equally susceptible to apoptosis induced by IL-2 withdrawal (data not shown).

Resistance to anti-Fas antibody-mediated apoptosis in RA lymphocytes is not attributable to reduced surface expression of the Fas receptor, since equivalent levels of Fas receptor expression could be found on lymphocytes of both the T and B cell lineage from normal individuals and RA patients. No differences in surface expression of CD4, CD8 or CD45RO could be detected between normal and RA T cells. Similarly, B cell lines from controls and RA patients expressed equivalent levels of CD30 and CD40 on their cell surface (data not shown).

Example 3

The above results suggest that an intracellular defect may be responsible for the observed resistance to apoptosis. The Fas-mediated signaling cascade is initiated by oligomerization of the intracytoplasmic death domain and assembly of a death signaling complex. Those events lead to activation of caspases such as Yama/CPP32 (caspase 3), that in turn cleave death substrates, including poly(ADP-ribose) polymerase (PARP) to a signature apoptotic form. Thus, examination of downstream proteolytic events following Fas ligation reports on the integrity of this pathway.

Figure 4A:
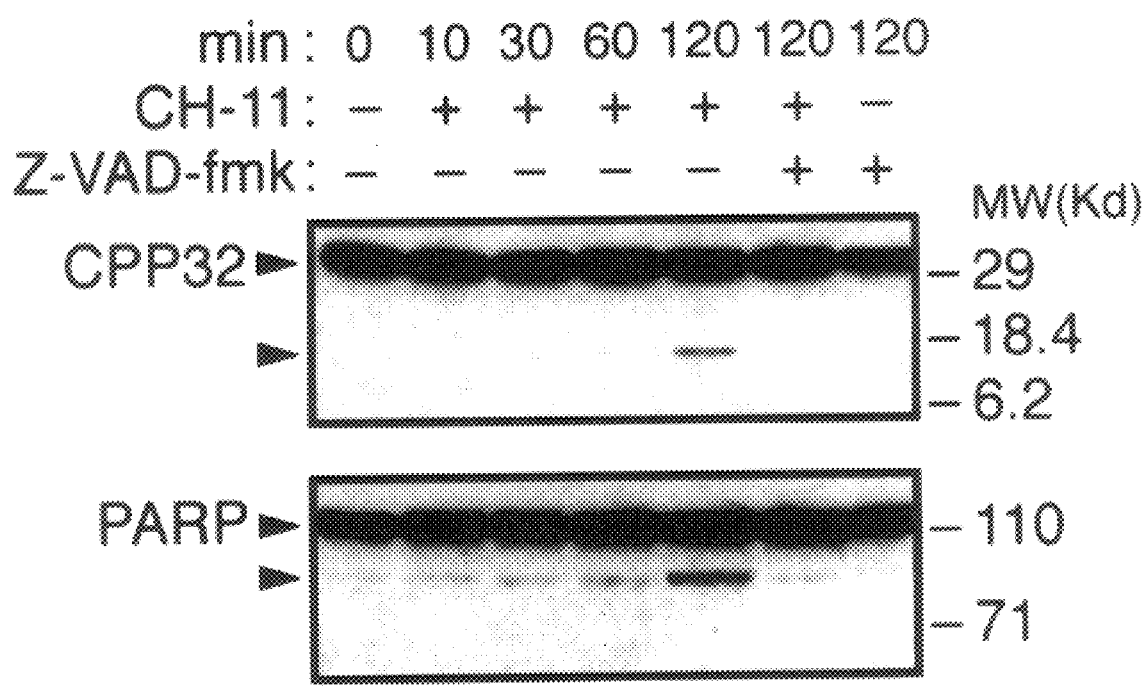
FIG. 4A shows photographs of two Western blots showing inhibition of proteolytic cleavage of CPP32 and PARP in normal cells.

In this example, it is demonstrated that activation of caspases is essential for Fas-mediated apoptosis. Briefly, cells were preincubated for 1 hr in the presence or absence of 40 μM of Z-VAD-fmk, and subsequently incubated with 100 ng/ml of the anti-Fas antibody H-11. At different time points thereafter, cells were collected, lysed and a Western blot analysis performed with the relevant antibodies. The results show the inhibitor Z-VAD-fmk blocks proteolytic processing of CPP32 (FIG. 4a, upper panel), cleavage of PARP (FIG. 4A, lower panel), and subsequent cell death.

Figure 4B:
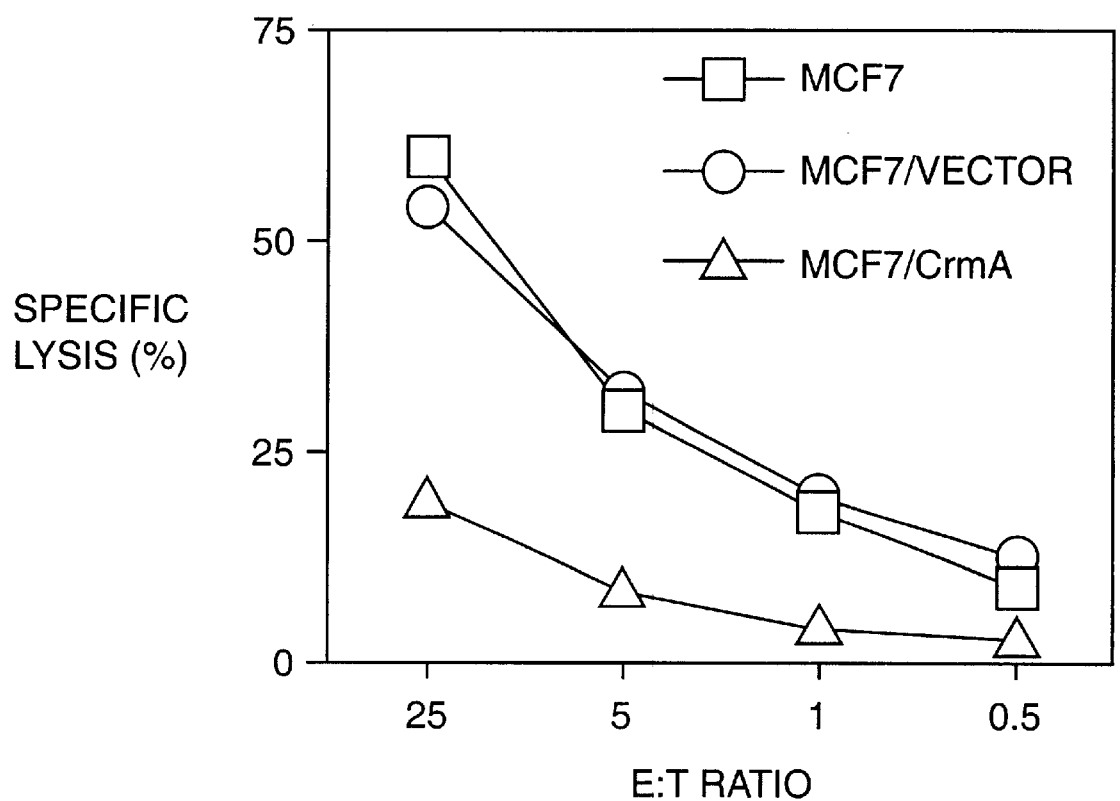
FIG. 4B is a graph showing the susceptibility of virus-infected cells to cytolysis.

The resistance of MCF7 targets transfected with crmA cDNA to killing by Vγ9/Vδ2 T cell clones was also tested. The results show that caspases are also essential for apoptotic killing mediated by cytolytic Vγ9/Vδ2 T cell clones, since MCF7 target cells expressing the cowpox virus crmA are resistant to cytolysis (FIG. 4B).

Figure 4C:
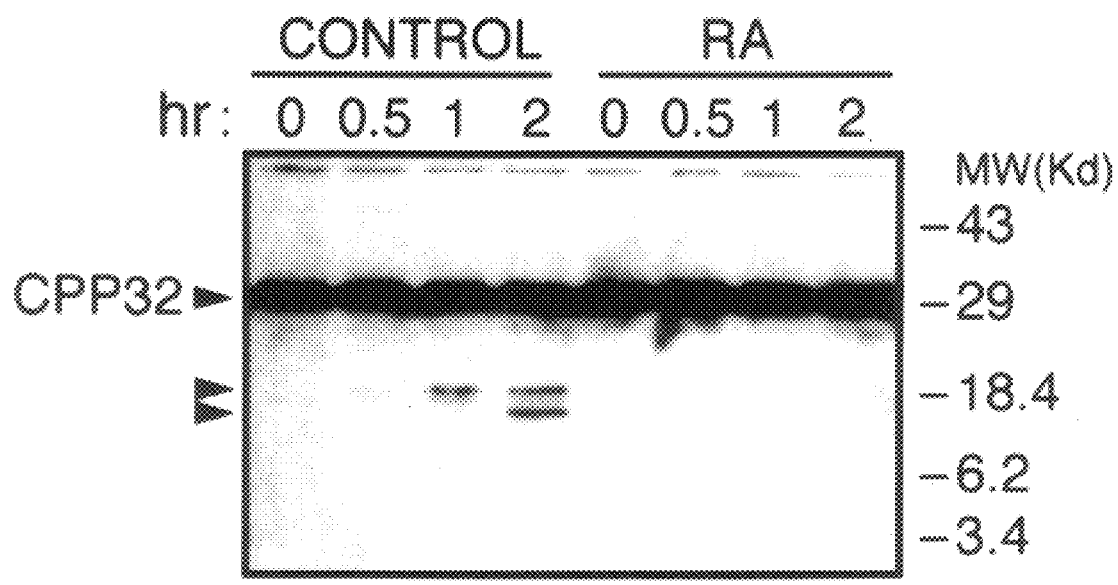
FIG. 4C shows a photograph of a Western blot showing proteolytic cleavage of CPP32 by normal cells but not by RA cells.
Figure 4D:
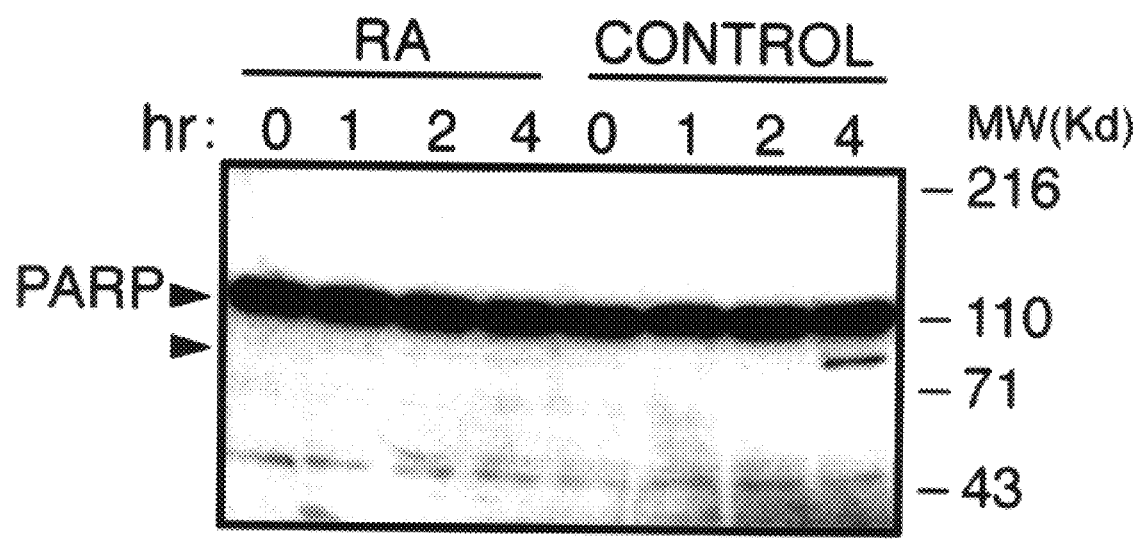
FIG. 4D shows a photograph of a Western blot showing proteolytic cleavage of PARP by normal cells but not by RA cells.

The Fas pathway in RA lymphocytes was also examined for impaired activation of caspases. Briefly, cells were incubated with 100 ng/ml of the anti-Fas antibody, CH-11, over a time course and Western blot analysis performed with the relevant antibodies. Examination of the Fas pathway in RA lymphocytes revealed impaired activation of caspases. In 4 of 4 normal lymphoblastoid B cell lines, but in none of 4 RA lines tested, proteolytic cleavage of CPP32 could be seen within 2 hours following Fas ligation (FIG. 4C). Similarly, cleavage of PARP was detected in normal lines within 1–4 hours, but was undetectable in lines from RA patients (FIG. 4lD). Cleavage of CP32 and PARP could be seen in RA lymphocytes at later time points (data not shown), suggesting that Fas-mediated signals are being transduced, albeit inefficiently.

Example 4

Figure 5A:
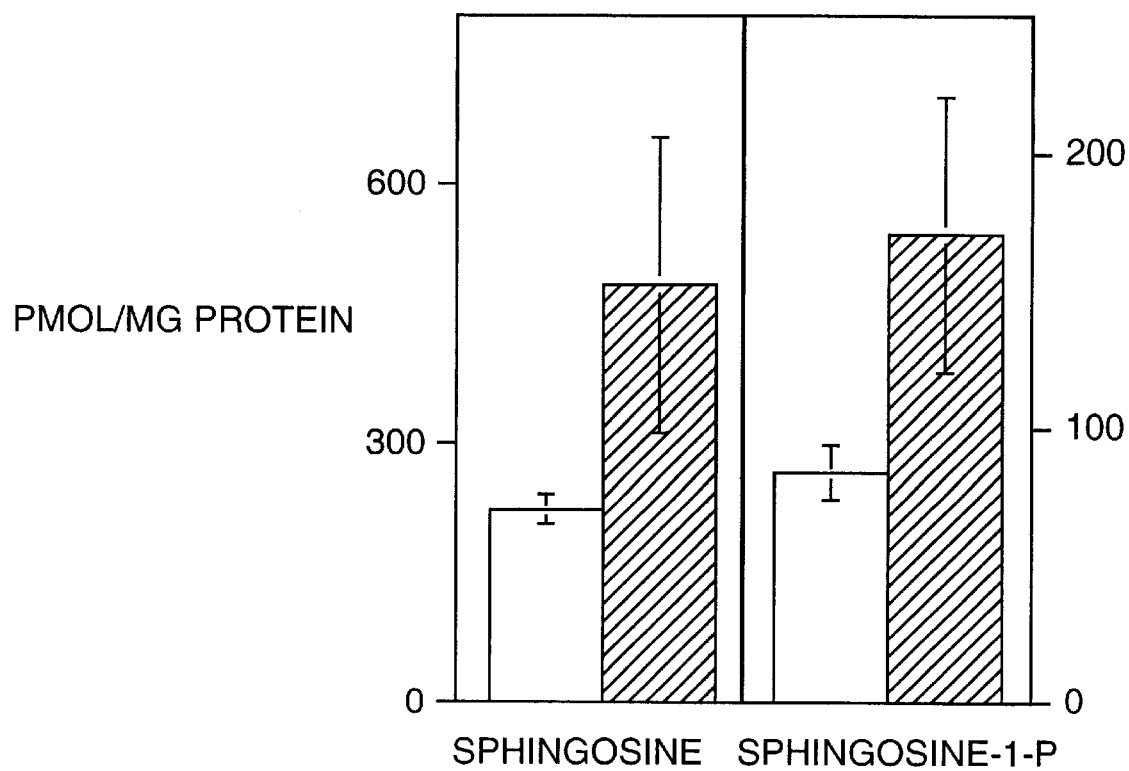
FIG. 5A is a bar graph showing constitutive levels of sphingosine and SPP in normal and RA patients.

To investigate the possibility that Fas-mediated signals are being modulated by an exogenous inhibitor, the sphingomyelin pathway was studied, which has been previously shown to regulate Fas-mediated apoptosis. No significant differences in either ceramide levels or sphingomyelinase activity could be found between control and RA lymphocytes (data not shown). However, when sphingosine and SPP levels were quantitatively measured by the conversion of SPP to tritiated N-acetyl-sphingosine-1-phosphate by acetylation with $^3$H acetic anhydride, intracellular levels of these 2 ceramide metabolites were found to be significantly higher in RA lymphocytes. FIG. 5A shows the constitutive levels of sphingosine (left) and SPP (right) in EBV transformed B cell lines from eight normal controls (open bar) and five RA patients (hatched bars).

Figure 5B:
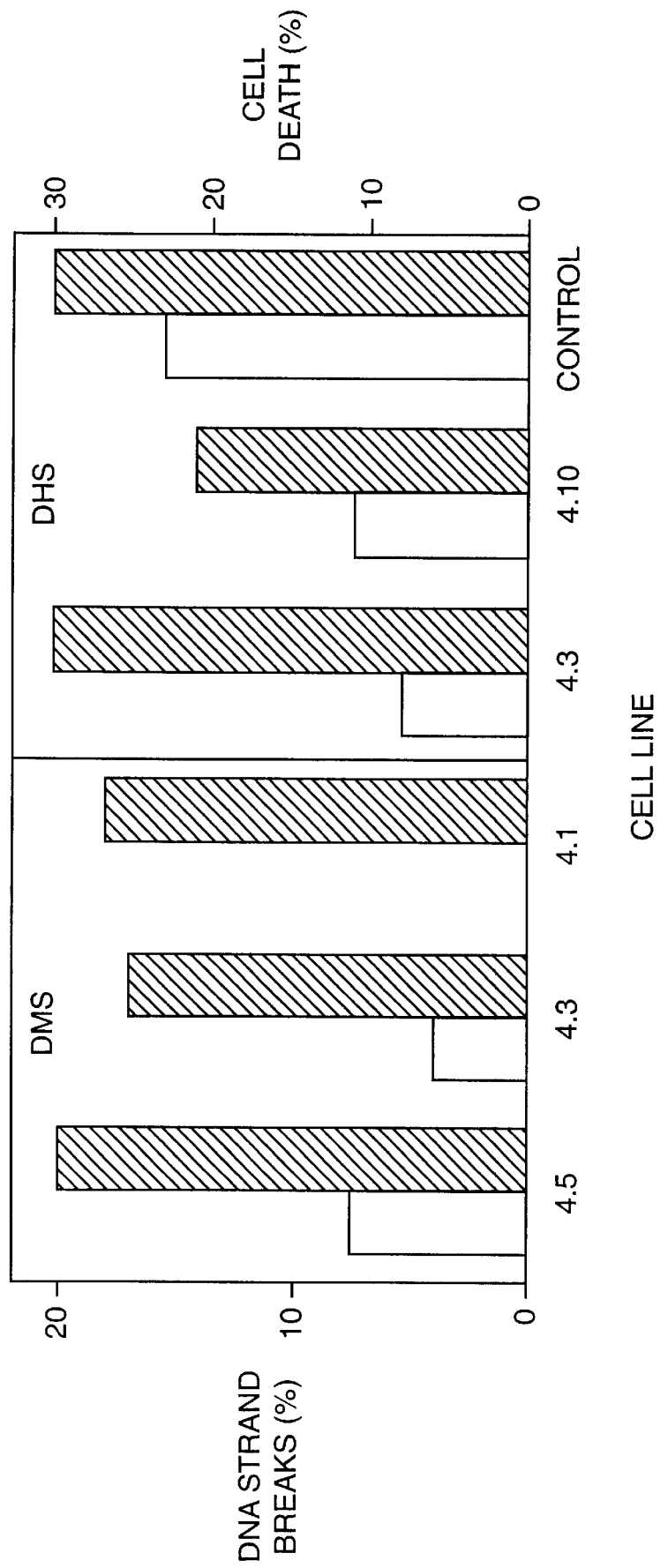
FIG. 5B is a bar graph showing reversal of resistance to Fas-mediated apoptosis by DMS and DHS.

SPP, a potent derivative of sphingosine, has been recently shown to activate a pertussis toxin-sensitive G protein and to inhibit Fas-mediated cell death, Therefore, the ability of SPP to inhibit apoptosis in RA lymphocytes was investigated Apoptosis induced by 8 hr stimulation with the anti-Fas antibody CH-11 (100 ng/ml) was determined in EBV transformed target cells in the presence FIG. 5B, dashed bars) or absence (FIG. 5B, open bars) of 2.5 μM DMS in serum-free RPMI 1640 medium supplemented with insulin and transferrin. At the end of incubation, cells were washed and DNA strand breaks were determined using the TUNEL assay. As can be seen, resistance of RA targets to apoptosis by anti-Fas antibodies could be effectively reversed by prior incubation of target cells with the sphingosine kinase inhibitors, N,N-dimethylsphingosine (DMS) or DL-threo-dihydrosphingosine (DHS).

Figure 5C:
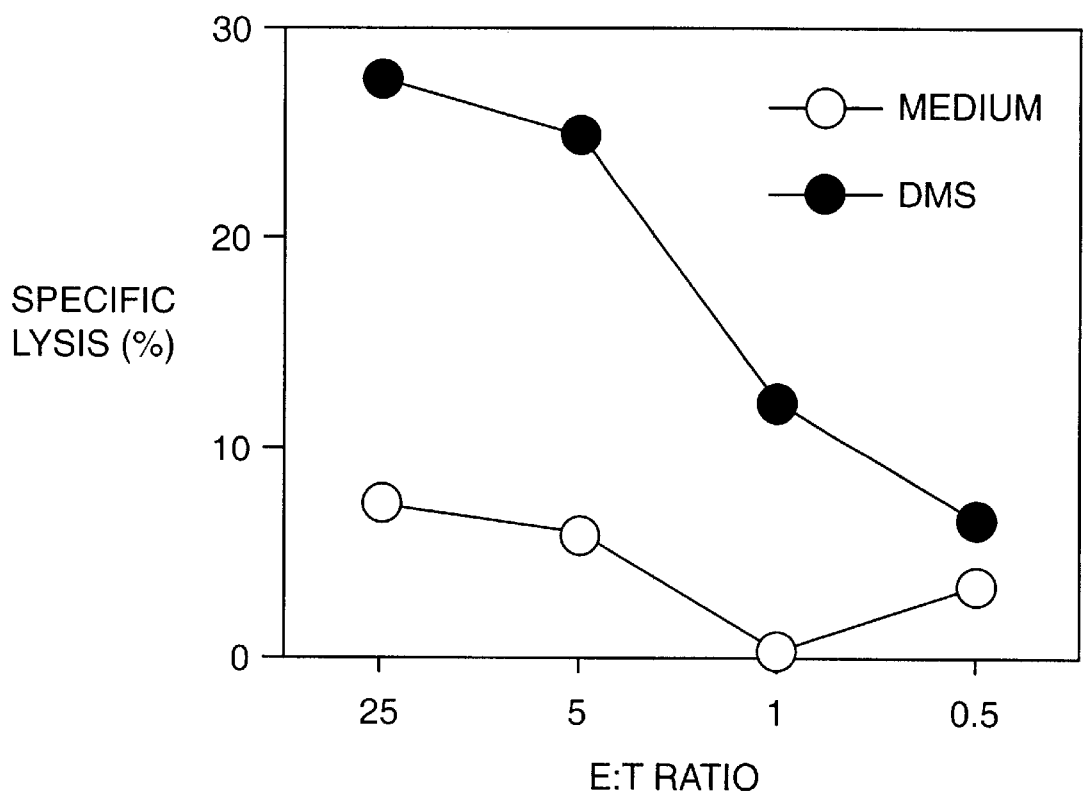
FIG. 5C is a graph showing reversal of resistance to T cell-mediated cytolysis in RA lymphocytes by DMS.

Inhibition of Fas-mediated death signaling by SPP was also examined using γδ F cell clones. Cytolysis of EBV transformed target cells by Vγ9/Vδ2 T cells was determined by 4 hr $^{51}$Cr release assay (FIG. 5C) in the presence (●) or absence (○) of 2.5 μM DMS. At the end of incubation, targets were washed and susceptibility to killing by γδ T cells was assessed. A representative experiment with one RA target, out of five tested is shown in FIG. 5C. As can be seen, resistance of RA targets to apoptosis by γδ T cells could be effectively reversed by prior incubation of target cells with the sphingosine kinase inhibitors, N,N-dimethylsphingosine (DMS) or DL-threo-dihydrosphingosine (DHS).

Figure 5D:
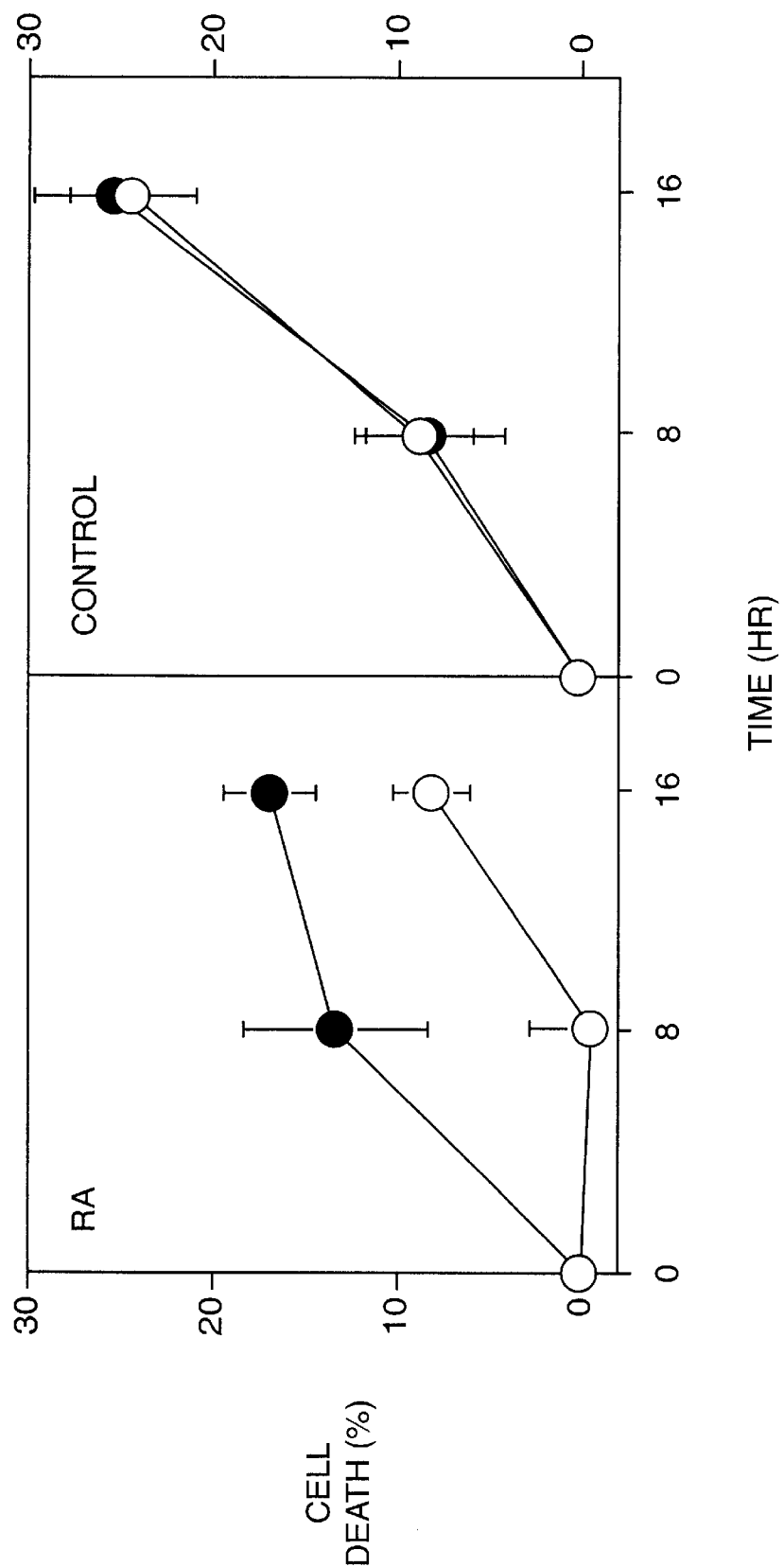
FIG. 5D is a graph showing reversal of resistance to Fas-mediated apoptosis by pertussis toxin.
Figure 5E:
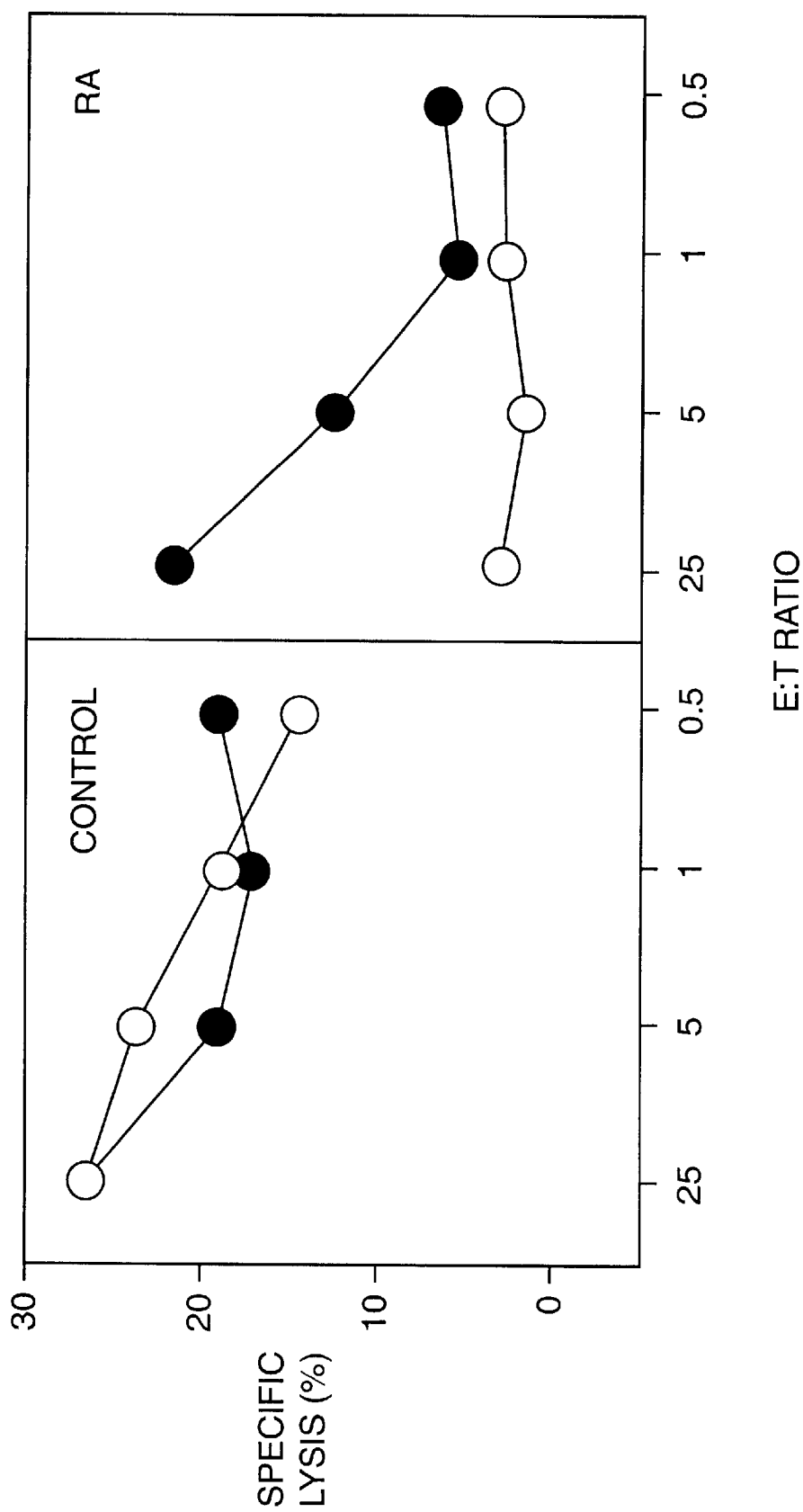
FIG. 5E is a graph showing reversal of resistance to cytolysis by pertussis toxin.

Additionally, pre-incubating RA targets with pertussis toxin reversed their resistance to Fas-mediated and γδ T cell-mediated killing (FIGS. 5D and 5E). For assessing Fas-mediated killing, EBV transformed B cell lines from eight normal controls (FIG. 5D, left) and six RA patients (FIG. 5E right) were preincubated with (●) or without (○) pertussis toxin, 1μg/ml for 1 hr. At the end of incubation, target cells were washed and stimulated with 100 ng/ml of the anti-Fas antibody CH-11 over a time course. Cell death was determined using the commercial MTS kit (Promega, Madison, Wis.). For assessing γδ T cell-mediated killing (FIG. 5E), EBV transformed B cell targets were incubated for 1 hr with (●) or without (○)) 1 μg/ml pertussis toxin as above. At the end of incubation, targets were washed and susceptibility to γδ T cell killing was determined using a 4 hr $^{51}$Cr-release assay.

Example 5

Figure 6:
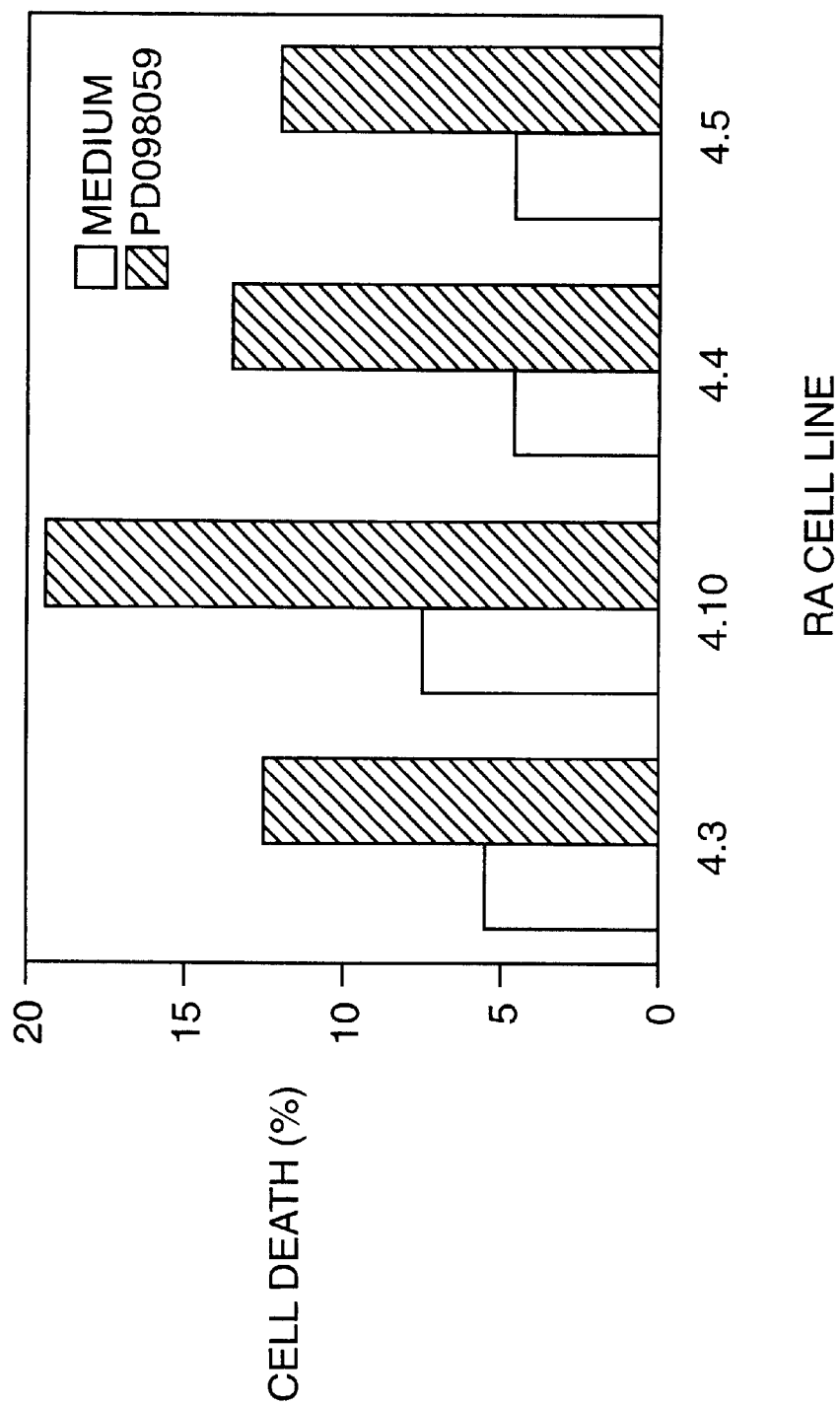
FIG. 6 is a bar graph showing reversal of resistance to Fas-mediated apoptosis by the MEK1 inhibitor, PD098059.

As noted above, it is not intended that the present invention be limited to any one inhibitor. In this example, resistance to Fas-mediated cell killing is shown to be reversed by preincubation of target cells with a MEK1 inhibitor. Apoptosis of RA EBV transformed target cells was induced by 16 hr stimulation with anti-Fas antibody CH-11 (200 ng/ml) in the presence (FIG. 6, black bars) or absence (FIG. 6, open bars) of 100 M of the MEK1 inhibitor 2-(2'-amino3'-methoxyphenyl-oxanaphthalen-4-one) (PD098059).

Example 6

In this example, inhibitors are tested in an animal model. RA-like disease is inducible in certain strains of rats (e.g.. Lewis rats) by immunization with *Mycobacterium tuberculosis* ("MT") in oil or CFA. See C. Jacob et al., "Heterogeneous Effects of IFN in Adjuvant Arthritis," *J. Immunol.* 142:1500 (1989). The disease is characterized by a self-limited, subacute polyarthritis and has been proposed as a model for human RA.

Rats are inoculated intradermally at the base of the tail with 0.1 ml CFA containing 10 mg/ml of heat killed MT in IFA (Difco Laboratories, Detroit, Mich.). Sphingosine derivatives (methylsphingosine, dimethylsphingosine and trimethylsphingosine in separate rats) are used as inhibitors of the sphingomyelin signal transduction pathway. The derivatives are prepared in a mixture containing a local anesthetic and injected intra-articularly. MT-reactive T cells from the joints are compared pre- and post-injection to assure that symptoms are reduced due to the administration of the inhibitor.

What is claimed is:

1. A composition, comprising at least one inhibitor of the sphingomyelin signal transduction pathway, selected from the group consisting of methylsphingosine, dimethylsphingosine, (1S,2R)-D-erythro-2-(N-myristoylamino)-phenyl-1-propanol, N-butyldeoxynojirimycin and 2-(2'-amino-3'-methoxyphenyl-oxanaphthalen-4-one) in combination with an anesthetic.

2. The composition of claim 1, wherein said anesthetic is a local anesthetic.

3. The composition of claim 2, wherein said local anesthetic is selected from a group comprising procaine and lidocaine.

4. The composition of claim 1, wherein said combination further comprises a pharmacologically acceptable carrier.

5. The composition of claim 1, wherein said combination is suitable for intra-articular injection.

* * * * *

UNITED STATES PATENT AND TRADEMARK OFFICE
CERTIFICATE OF CORRECTION

| | | |
|---|---|---|
| PATENT NO. | : 6,518,259 B1 | Page 1 of 1 |
| APPLICATION NO. | : 09/575612 | |
| DATED | : February 11, 2003 | |
| INVENTOR(S) | : Joseph Holoshitz, James A. Shayman and Shi-Yu Tan | |

It is certified that error appears in the above-identified patent and that said Letters Patent is hereby corrected as shown below:

Col. 1, line 1, add:

--This invention was made with government support under AR41073 and AR43999 awarded by NIH. The government has certain rights in the invention.--

Signed and Sealed this

Sixth Day of February, 2007

JON W. DUDAS
*Director of the United States Patent and Trademark Office*